(12) United States Patent
Holub et al.

(10) Patent No.: US 10,562,871 B2
(45) Date of Patent: *Feb. 18, 2020

(54) SYNTHESIS OF SULFUR CONTAINING AMMONIUM AND PHOSPHONIUM BORATES

(71) Applicant: Gotion Inc., Fremont, CA (US)

(72) Inventors: Nicole Holub, Mannheim (DE); Juergen Herbel, Mannheim (DE)

(73) Assignee: Gotion Inc., Fremont, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/119,374

(22) Filed: Aug. 31, 2018

(65) Prior Publication Data

US 2019/0194153 A1 Jun. 27, 2019

Related U.S. Application Data

(63) Continuation of application No. 15/549,409, filed as application No. PCT/EP2016/052529 on Feb. 5, 2016, now Pat. No. 10,065,936.

(30) Foreign Application Priority Data

Feb. 9, 2015 (EP) .................................... 15154303

(51) Int. Cl.
 *C07D 295/088* (2006.01)
 *C07F 5/04* (2006.01)
 *C07C 303/32* (2006.01)
 *C07F 5/02* (2006.01)

(52) U.S. Cl.
 CPC ........ *C07D 295/088* (2013.01); *C07C 303/32* (2013.01); *C07F 5/022* (2013.01); *C07F 5/04* (2013.01)

(58) Field of Classification Search
 CPC ... C07C 303/32; C07D 295/088; C07F 5/022; C07F 5/04
 See application file for complete search history.

(56) References Cited

U.S. PATENT DOCUMENTS 10,065,936 B2 * 9/2018 Holub ................ C07D 295/088

* cited by examiner

*Primary Examiner* — Valerie Rodriguez-Garcia
(74) *Attorney, Agent, or Firm* — Young Basile Hanlon & MacFarlane, P.C.

(57) ABSTRACT

The present disclosure relates to the preparation of sulfur containing ammonium and phosphonium borates KA, wherein K is a compound of formula (I), and A is an anion of formulae (IIa) or (IIb) by bringing into contact ammonium borates with sulfur containing ammonium or phosphonium halides or sulfonates.

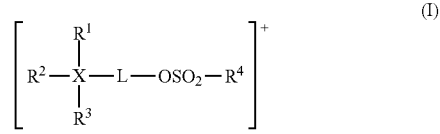

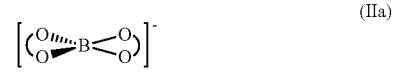

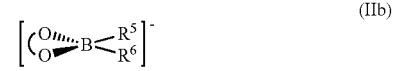

14 Claims, No Drawings

SYNTHESIS OF SULFUR CONTAINING AMMONIUM AND PHOSPHONIUM BORATES

CROSS-REFERENCE TO RELATED APPLICATION

This application is a continuation of application Ser. No. 15/549,409, filed on Aug. 8, 2017, which is a 371 application of International Application No. PCT/EP2016/052529, filed Feb. 5, 2016, which claims priority to EP Application No. 15154303.0, filed on Feb. 9, 2015, the contents of all of which are herein incorporated by reference in their entireties.

DESCRIPTION

The present invention relates to the preparation of sulfur containing ammonium borates.

Sulfur containing additives comprising sulfur containing ammonium and phosphonium cations and various anions including borates and their application in electrolyte compositions for electrochemical cells are described in WO 2013/026854 A1. According to WO 2013/026854 A1 the sulfur containing additives containing a borate anion like bisoxalato borate are prepared via metathesis of an ionic compound containing a sulfur containing ammonium or phosphonium cation and a halide anion with an alkali salt of the borate anion, e.g. lithium bisoxalato borate.

The use of non-substituted tetraalkyl ammonium borate salts in electrolytes in galvanic cells is known from WO 94/27335 A1. WO 94/27335 A1 describes the preparation of the tetraalkyl ammonium borates by reaction of lithium hydroxide or tetraalkylammonium hydroxide with $B(OH)_3$ and the desired bidente ligand salicylic acid or catechin. WO 94/27335 A1 also discloses the synthesis of the ammonium borates via metathesis of the lithium borate salt with a tetraalkylammonium halide.

Up to now lithium borate is an expensive raw material. It was an object of the present invention to provide a process for preparing sulfur containing ammonium and phosphonium borates which can be used as alternative to the known processes and which does not require the lithium borate salts. The process shall be cost effective, should allow the use of educts which are easy to prepare, and should allow the efficient preparation of sulfur containing ammonium and phosphonium borates.

This object is achieved by process for preparing a compound KA comprising step (b) bringing into contact a compound $KA^1$ with a compound $K^1A$ in the presence of a solvent or solvent mixture (i),
wherein
K is a cation of formula (I)

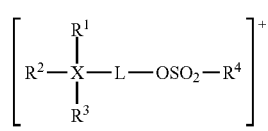

wherein
X is N or P;
$R^1$, $R^2$, and $R^3$ are selected independently from each other from $C_1$-$C_{10}$ alkyl, $C_2$-$C_{10}$ alkenyl, $C_2$-$C_{10}$ alkynyl, $C_6$-$C_{12}$ aryl, and $C_7$-$C_{24}$ aralkyl, which may be substituted by one or more groups selected from F, cyclopropyl, 1,2-epoxyethyl, and sulfonate, and wherein one or more $CH_2$ groups of alkyl, alkenyl, alkynyl and aralkyl which are not directly bound to the X-atom may be replaced by O, 1,2-epoxyethylene, cyclopropylene, $OSO_2$ or $SO_2O$;
or wherein $R^1$ and $R^2$ are linked and jointly selected from —$(CH_2)_m$— alkylene with m=4 or 5 forming together with the central X-atom a five- or six-membered heterocycle wherein one or more H of —$(CH_2)_m$— alkylene may be replaced by one or more substituents selected from F and optionally fluorinated $C_1$-$C_{10}$ alkyl, and wherein one or more $CH_2$ groups of —$(CH_2)_m$ alkylene may be replaced by O, S or NR';
R' is selected from H, $C_1$-$C_{10}$ alkyl, $C_2$-$C_{10}$ alkenyl, $C_2$-$C_{10}$ alkynyl, $C_6$-$C_{12}$ aryl, and $C_7$-$C_{24}$ aralkyl, which may be substituted by one or more groups selected from F, cyclopropyl, 1,2-epoxyethyl, and sulfonate, and wherein one or more $CH_2$ groups of alkyl, alkenyl, alkynyl and aralkyl which are not directly bound to the N-atom may be replaced by O, 1,2-epoxyethylene, cyclopropylene, $OSO_2$ or $SO_2O$;
L is a —$(CH_2)_n$— chain wherein one or more $CH_2$ groups of the —$(CH_2)_n$— chain which are not directly bound to the X-atom or the $OSO_2$ group may be replaced by O and wherein a C—C single bond between two adjacent $CH_2$ groups of the —$(CH_2)_n$-chain may be replaced by a C—C double bond or a C—C triple bond;
n is an integer from 1 to 8;
$R^4$ is selected from $C_1$-$C_{20}$ alkyl, $C_2$-$C_{20}$ alkenyl, $C_2$-$C_{20}$ alkynyl, $C_6$-$C_{12}$ aryl, and $C_7$-$C_{24}$ aralkyl, which may be substituted by one or more groups selected from F, cyclopropyl, 1,2-epoxyethyl, and sulfonate, and wherein one or more $CH_2$ groups of alkyl, alkenyl, alkynyl and aralkyl which are not directly bound to the $OSO_2$ group may be replaced by O, 1,2-epoxyethylene, cyclopropylene, $OSO_2$ or $SO_2O$;
A is an anion of formulae (IIa) or (IIb)

wherein
$R^5$ and $R^6$ independently from each other are selected from F, $C_1$-$C_{20}$ alkyl, $OC_1$-$C_{20}$ alkyl, and $OC(O)C_1$-$C_{20}$ alkyl, wherein alkyl may be substituted by one or more F;

independently at each occurrence is a bidentate radical derived from a 1,2- or 1,3-diol, from a 1,2- or 1,3-dicarboxylic acid or from a 1,2- or 1,3-hydroxycarboxylic acid by abstracting the two H atoms of pairs of adjacent OH groups in 1,2- or 1,3-position;
$A^1$ is an anion selected from $[R^7—SO_3]^-$, $Cl^-$, $Br^-$, and $I^-$,
wherein
$R^7$ is selected from $C_1$-$C_{20}$ alkyl, $C_2$-$C_{20}$ alkenyl, $C_2$-$C_{20}$ alkynyl, $C_6$-$C_{12}$ aryl, and $C_7$-$C_{24}$ aralkyl, which may be substituted by one or more groups selected from F, cyclopropyl, 1,2-epoxyethyl, and sulfonate, and wherein one or more CH$_2$ groups of alkyl, alkenyl, alkynyl and aralkyl which are not directly bound to the SO$_3$ group may be replaced by O, 1,2-epoxyethylene, cyclopropylene, OSO$_2$ or SO$_2$O; and K$^1$ is a cation selected from [NR$^8$R$^9$R$^{10}$R$^{11}$]$^+$, wherein R$^8$, R$^9$, and R$^{10}$ are selected independently from each other from C$_1$-C$_{10}$ alkyl or wherein R$^8$ and R$^9$ are linked and jointly selected from —(CH$_2$)$_p$— alkylene with p=4 or 5 forming together with the central N-atom a five- or six-membered heterocycle wherein one or more H of —(CH$_2$)$_p$— alkylene may be replaced by one or more substituents selected from C$_1$-C$_{10}$ alkyl, and wherein one or more CH$_2$ groups of —(CH$_2$)$_p$— alkylene may be replaced by O, N or NR'', R'' is selected from H and C$_1$-C$_{10}$ alkyl, and R$^{11}$ is selected independently from R$^8$, R$^9$, and R$^{10}$ from H and C$_1$-C$_{10}$ alkyl.

The term "C$_1$-C$_{20}$ alkyl" as used herein means a straight or branched saturated hydrocarbon group with 1 to 20 carbon atoms having one free valence and includes, e.g., methyl, ethyl, n-propyl, isopropyl, n-butyl, sec-butyl, isobutyl, tert-butyl, n-pentyl, iso-pentyl, 2,2-dimethylpropyl, n-hexyl, iso-hexyl, 2-ethyl hexyl, n-heptyl, iso-heptyl, n-octyl, iso-octyl, n-nonyl, n-decyl and the like. Preferred are C$_1$-C$_{10}$ alkyl groups, more preferred are C$_1$-C$_6$ alkyl groups, even more preferred are C$_1$-C$_4$ alkyl groups, and most preferred are methyl, ethyl, and 1- and 2-propyl.

The term "C$_2$-C$_{20}$ alkenyl" as used herein refers to an unsaturated straight or branched hydrocarbon group with 2 to 20 carbon atoms having one free valence. Unsaturated means that the alkenyl group contains at least one C—C double bond. C$_2$-C$_{20}$ alkenyl includes for example ethenyl, 1-propenyl, 2-propenyl, 1-n-butenyl, 2-n-butenyl, iso-butenyl, 1-pentenyl, 1-hexenyl, 1-heptenyl, 1-octenyl, 1-nonenyl, 1-decenyl and the like. Preferred are C$_2$-C$_{10}$ alkenyl groups, more preferred are C$_2$-C$_6$ alkenyl groups, even more preferred are C$_2$-C$_4$ alkenyl groups and in particular preferred are ethenyl and 1-propen-3-yl (allyl).

The term "C$_2$-C$_{20}$ alkynyl" as used herein refers to an unsaturated straight or branched hydrocarbon group with 2 to 20 carbon atoms having one free valence, wherein the hydrocarbon group contains at least one C—C triple bond. C$_2$-C$_{20}$ alkynyl includes for example ethynyl, 1-propynyl, 2-propynyl, 1-n-butynyl, 2-n-butynyl, iso-butynyl, 1-pentynyl, 1-hexynyl, -heptynyl, 1-octynyl, 1-nonynyl, 1-decynyl and the like. Preferred are C$_2$-C$_{10}$ alkynyl, more preferred are C$_2$-C$_6$ alkynyl, even more preferred are C$_2$-C$_4$ alkynyl, in particular preferred are ethynyl and 1-propyn-3-yl (propargyl).

The term "C$_6$-C$_{12}$ aryl" as used herein denotes an aromatic 6- to 12-membered hydrocarbon cycle or condensed cycles having one free valence. Examples of C$_6$-C$_{12}$ aryl are phenyl and naphtyl. Preferred is phenyl.

The term "C$_7$-C$_{24}$ aralkyl" as used herein denotes an aromatic 6- to 12-membered aromatic hydrocarbon cycle or condensed aromatic cycles substituted by one or more C$_1$-C$_6$ alkyl. The C$_7$-C$_{24}$ aralkyl group contains in total 7 to 24 C-atoms and has one free valence. The free valence may be located at the aromatic cycle or at a C$_1$-C$_6$ alkyl group, i.e. C$_7$-C$_{24}$ aralkyl group may be bound via the aromatic part or via the alkyl part of the aralkyl group. Examples of C$_7$-C$_{24}$ aralkyl are methylphenyl, 1,2-dimethylphenyl, 1,3-dimethylphenyl, 1,4-dimethylphenyl, ethylphenyl, 2-propylphenyl, and the like.

The term "sulfonate" as used herein means the groups —S(O)$_2$O—R''' or —OS(O)$_2$—R''' wherein R''' is selected from C$_1$-C$_{10}$ alkyl, preferably from C$_1$-C$_6$ alkyl and more preferred from C$_1$-C$_4$ alkyl.

The term "cyclopropylene" as used herein means the group derived from cyclo-propane molecule having two free valences at two adjacent C-atoms:

the asterisks denote the two free valences.

The term "1,2-epoxyethyl" as used herein means an oxirane cycle having one free valence:

the asterisk denotes the free valence.

The term "1,2-epoxyethylene" as used herein means an oxirane cycle having two free valences at the two adjacent C-atoms:

the asterisks denote the free valences.

The sulfur containing ammonium borates KA are prepared by bringing into contact compounds K$^1$A with compounds KA$^1$ in the presence of a solvent or solvent mixture (i). No lithium borate salt has to be used. The ammonium borate salt K$^1$A is easily obtainable and less expensive than the analogue lithium borate salts.

In the following the invention is described in detail.

K is a sulfur containing cation of formula (I) as defined above.

X is N or P; preferably X is N.

R$^1$, R$^2$, and R$^3$ are selected independently from each other from C$_1$-C$_{10}$ alkyl, C$_2$-C$_{10}$ alkenyl, C$_2$-C$_{10}$ alkynyl, C$_6$-C$_{12}$ aryl, and C$_7$-C$_{24}$ aralkyl, which may be substituted by one or more groups selected from F, cyclopropyl, 1,2-epoxyethyl, and sulfonate, and wherein one or more CH$_2$ groups of alkyl, alkenyl, alkynyl and aralkyl which are not directly bound to the X-atom may be replaced by O, 1,2-epoxyethylene, cyclopropylene, OSO$_2$ or SO$_2$O; or R$^1$ and R$^2$ are linked and jointly selected from —(CH$_2$)$_m$— alkylene with m=4 or 5 forming together with the central X-atom a five- or six-membered heterocycle wherein one or more H of —(CH$_2$)$_m$— alkylene may be replaced by one or more substituents selected from F and optionally fluorinated C$_1$-C$_{10}$ alkyl, and wherein one or more CH$_2$ groups of —(CH$_2$)$_m$— alkylene may be replaced by O, S or NR'.

The five- or six-membered heterocycle formed by R$^1$ and R$^2$ and the central X-atom may be selected for example from

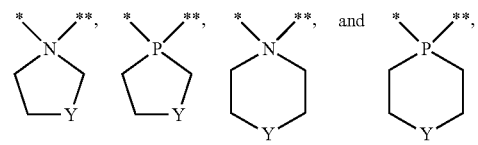

wherein Y is CH$_2$, O, S or NR' and the asterisks denote the bonds to L and R$^3$, respectively. Examples of five- or six-membered heterocycles formed by $R^1$ and $R^2$ and the central X-atom are pyrrolidine, piperidine, and morpholine.

If $R^1$ and $R^2$ are not linked, $R^1$ and $R^2$ are preferably selected independently from each other from $C_1$-$C_6$ alkyl, $C_2$-$C_6$ alkenyl, $C_2$-$C_6$ alkynyl, $C_6$-$C_{12}$ aryl, and $C_7$-$C_{18}$ aralkyl, and more preferred from $C_1$-$C_4$ alkyl, $C_2$-$C_4$ alkenyl, $C_2$-$C_4$ alkynyl, $C_6$-$C_{12}$ aryl, and $C_7$-$C_{14}$ aralkyl, and most preferred from $C_1$-$C_4$ alkyl, $C_2$-$C_4$ alkenyl, $C_2$-$C_4$ alkynyl, wherein alkyl, alkenyl, alkynyl, aryl and aralkyl may be substituted one or more groups selected from F, cyclopropyl, 1,2-epoxyethyl and sulfonate, and wherein one or more $CH_2$ group of alkyl, alkenyl, alkynyl and aralkyl which are not directly bound to the X-atom may be replaced by O, 1,2-epoxyethylene, cyclopropylene, $OSO_2$ or $SO_2O$.

If $R^1$ and $R^2$ are linked they are preferably jointly selected from —$(CH_2)_4$— alkylene forming together with the central X-atom a five-membered heterocycle wherein one or more H of —$(CH_2)_4$— alkylene may be substituted by one or more substituents selected from F and optionally fluorinated $C_1$-$C_{10}$ alkyl, preferably from F and optionally fluorinated $C_1$-$C_4$ alkyl, and wherein one or more $CH_2$ groups of —$(CH_2)_4$— alkylene may be replaced by O, S or NR'. The preferred five-membered heterocycle formed by $R^1$ and $R^2$ and the central X-atom is pyrrolidine.

$R^1$ and $R^2$ are preferably linked and jointly selected from —$(CH_2)_m$— alkylene with m=4 or 5 forming together with the central X-atom a five- or six-membered heterocycle, wherein one or more H of —$(CH_2)_m$— alkylene may be replaced by one or more substituents selected from F and optionally fluorinated $C_1$-$C_{10}$ alkyl, and wherein one or more $CH_2$ groups of —$(CH_2)_m$— alkylene may be replaced by O, S or NR', more preferred m is 4.

$R^3$ is selected independently from $R^1$ and $R^2$ from $C_1$-$C_{10}$ alkyl, $C_2$-$C_{10}$ alkenyl, $C_2$-$C_{10}$ alkynyl, $C_6$-$C_{12}$ aryl, and $C_6$-$C_{24}$ aralkyl, preferably from $C_1$-$C_6$ alkyl, $C_2$-$C_6$ alkenyl, $C_2$-$C_6$ alkynyl, $C_6$-$C_{12}$ aryl, and $C_7$-$C_{18}$ aralkyl, more preferred from $C_1$-$C_6$ alkyl, $C_2$-$C_6$ alkenyl, and $C_2$-$C_6$ alkynyl, wherein alkyl, alkenyl, alkynyl, aryl and aralkyl may substituted one or more groups selected from F, cyclopropyl, 1,2-epoxyethyl, and sulfonate, and wherein one or more $CH_2$ groups of alkyl, alkenyl, alkynyl and aralkyl which are not directly bound to the X-atom may be replaced by O, 1,2-epoxyethylene, cyclopropylene or $SO_3$, preferably by O or $SO_3$. Even more preferred $R^3$ is methyl, ethyl or propyl, most preferred $R^3$ is methyl.

L is a —$(CH_2)_n$— chain wherein one or more $CH_2$ groups of the —$(CH_2)_n$— chain which are not directly bound to the X-atom or the $OSO_2$ group may be replaced by O and wherein a C—C single bond between two adjacent $CH_2$ groups of the —$(CH_2)_n$-chain may be replaced by a C═C double bond or a C≡C triple bond.

n is an integer selected from 1, 2, 3, 4, 5, 6, 7, and 8, preferably n is 1, 2, 3 or 4, more preferred n is 2, 3 or 4.

Preferably L is a non-substituted alkylene chain with n being selected as defined above.

$R^4$ is selected from $C_1$-$C_{20}$ alkyl, $C_2$-$C_{20}$ alkenyl, $C_2$-$C_{20}$ alkynyl, $C_6$-$C_{12}$ aryl, and $C_7$-$C_{24}$ aralkyl, preferably $R^4$ is selected from $C_1$-$C_{10}$ alkyl, $C_2$-$C_{10}$ alkenyl, $C_2$-$C_{10}$ alkynyl, $C_6$-$C_{12}$ aryl, and $C_7$-$C_{24}$ aralkyl, and more preferred $C_1$-$C_6$ alkyl, $C_2$-$C_6$ alkenyl, $C_2$-$C_6$ alkynyl, $C_6$-$C_{12}$ aryl, and $C_7$-$C_{24}$ aralkyl, which may be substituted by one or more groups selected from F, cyclopropyl, 1,2-epoxyethyl, and sulfonate, and wherein one or more $CH_2$ groups of alkyl, alkenyl, alkynyl and aralkyl which are not directly bound to the $OSO_2$ group may be replaced by O, 1,2-epoxyethylene, cyclopropylene, $OSO_2$ or $SO_2O$; in particular preferred $R^4$ is selected from methyl, ethyl, propyl, ethenyl, 1-propen-3-yl ethynyl and 1-propyn-3-yl.

A is a borate anion of formula (IIa) or (IIb) as defined above.

$R^5$ and $R^6$ are selected independently from each other from F, $C_1$-$C_{20}$ alkyl, $OC_1$-$C_{20}$ alkyl, and $OC(O)C_1$-$C_{20}$ alkyl, wherein alkyl may be substituted by one or more F; preferably $R^5$ and $R^6$ are selected independently from each other from F, $C_1$-$C_6$ alkyl, $OC_1$-$C_6$ alkyl, and $OC(O)C_1$-$C_6$ alkyl, wherein alkyl may be substituted by one or more F, more preferred $R^5$ and $R^6$ are selected independently from each other from F, $C_1$-$C_4$ alkyl, $OC_1$-$C_4$ alkyl, and $OC(O)$ $C_1$-$C_4$ alkyl, wherein alkyl may be substituted by one or more F, and most preferred $R^5$ and $R^6$ are F.

is independently at each occurrence a bidentate radical derived from a 1,2- or 1,3-diol, from a 1,2- or 1,3-dicarboxylic acid or from a 1,2- or 1,3-hydroxycarboxylic acid by abstracting the two H atoms of pairs of adjacent OH groups in 1,2- or 1,3-position.

Suited 1,2- and 1,3-diols from which the bidentate radical is derived may be aliphatic or aromatic and are optionally substituted by one or more F and/or by at least one straight or branched non-fluorinated, partly fluorinated or fully fluorinated $C_1$-$C_4$ alkyl group. They may be selected, e.g., from 1,2-dihydroxybenzene, propane-1,2-diol, butane-1,2-diol, propane-1,3-diol, butan-1,3-diol, cyclohexyl-trans-1,2-diol and naphthalene-2,3-diol which are optionally are substituted by one or more F and/or by at least one straight or branched non-fluorinated, partly fluorinated or fully fluorinated $C_1$-$C_4$ alkyl group. An example for such 1,2- or 1,3-diole is 1,1,2,2-tetra(trifluoromethyl)-1,2-ethane diol. "Fully fluorinated $C_1$-$C_4$ alkyl group" means, that all H-atoms of the alkyl group are substituted by F.

Suited 1,2- or 1,3-dicarboxlic acids from which the bidentate radical is derived may be aliphatic or aromatic, for example oxalic acid, malonic acid (propane-1,3-dicarboxylic acid), phthalic acid or isophthalic acid, preferred is oxalic acid. The 1,2- or 1,3-dicarboxlic acid are optionally substituted by one or more F and/or by at least one straight or branched non-fluorinated, partly fluorinated or fully fluorinated $C_1$-$C_4$ alkyl group.

Suited 1,2- or 1,3-hydroxycarboxylic acids from which the bidentate radical is derived may be aliphatic or aromatic and are optionally substituted by one or more F and/or by at least one straight or branched non-fluorinated, partly fluorinated or fully fluorinated $C_1$-$C_4$ alkyl group. Examples of such 1,2- or 1,3-hydroxycarboxylic acids are salicylic acid, tetrahydro salicylic acid, malic acid, and 2-hydroxy acetic acid, which are optionally substituted by one or more F and/or by at least one straight or branched non-fluorinated, partly fluorinated or fully fluorinated $C_1$-$C_4$ alkyl group. An example for such 1,2- or 1,3-hydroxycarboxylic acids is 2,2-bis(trifluoromethyl)-2-hydroxy-acetic acid.

Examples of borate anions are bis-1,2-benzenediolato borate, bissalicylato borate, difluoro oxalato borate, and bisoxalato borate. Preferably A is selected from difluoro oxalato borate and bisoxalato borate.

Compounds of formula KA are described in detail in the not yet published European patent application EP 14163429.5.

$K^1$ is a cation selected from $[NR^8R^9R^{10}R^{11}]^+$ wherein $R^8$, $R^9$, and $R^{10}$ are selected independently from each other from $C_1$-$C_{10}$ alkyl, preferably $C_1$-$C_6$ alkyl and most preferred from $C_1$-$C_4$ alkyl, or wherein $R^8$ and $R^9$ are linked and jointly selected from —$(CH_2)_p$— alkylene with p=4 or 5, preferably p=4, forming together with the central N-atom a five- or six-membered heterocycle wherein one or more H of —$(CH_2)_p$— alkylene may be replaced by one or more substituents selected from $C_1$-$C_{10}$ alkyl, preferably $C_1$-$C_6$ alkyl and most preferred from $C_1$-$C_4$ alkyl, and wherein one or more $CH_2$ groups of —$(CH_2)_p$— alkylene may be replaced by O, N or NR", and R" is selected from H and $C_1$-$C_{10}$ alkyl, preferably from H and $C_1$-$C_6$ alkyl, and most preferred from H and $C_1$-$C_4$ alkyl, and $R^{11}$ is selected independently from $R^8$, $R^9$, and $R^{10}$ from H and $C_1$-$C_{10}$ alkyl, preferably $R^{11}$ is selected from H and $C_1$-$C_6$ alkyl, more preferred from H and $C_1$-$C_4$ alkyl, most preferred $R^{11}$ is H.

Preferably $R^8$, $R^9$, and $R^{10}$ are same and selected from $C_1$-$C_4$ alkyl or $R^8$ and $R^9$ are linked and jointly selected from —$(CH_2)_4$— alkylene forming together with the central N-atom a five-membered saturated or aromatic heterocycle wherein one or more H of —$(CH_2)_4$— alkylene may be replaced by one or more substituents selected from $C_1$-$C_4$ alkyl, and wherein one or more $CH_2$ groups of —$(CH_2)_4$— alkylene may be replaced by O, N or NR" with R" is selected from $C_1$-$C_4$ alkyl and $R^{10}$ is selected from $C_1$- to $C_4$ alkyl, and $R^{11}$ is selected independently from $R^8$, $R^9$, and $R^{10}$ from $C_1$-$C_4$ alkyl and H, preferably $R^{11}$ is H.

In a preferred embodiment $R^{11}$ is H and $K^1$ is a cation selected from $[HNR^8R^9R^{10}]^+$ wherein $R^8$, $R^9$, and $R^{10}$ are selected independently from each other as defined above.

The anion $A^1$ is preferably selected from $[R^7—SO_3]$— more preferred from $[R^7—SO_3]$ wherein $R^7$ is selected from $C_1$-$C_{10}$ alkyl, $C_2$-$C_{10}$ alkenyl, $C_2$-$C_{10}$ alkynyl, $C_6$-$C_{12}$ aryl, and $C_7$-$C_{24}$ aralkyl, and more preferred from $C_1$-$C_6$ alkyl, $C_2$-$C_6$ alkenyl, $C_2$-$C_6$ alkynyl, $C_6$-$C_{12}$ aryl, and $C_7$-$C_{24}$ aralkyl, which may be substituted by one or more groups selected from F, cyclopropyl, 1,2-epoxyethyl, and sulfonate, and wherein one or more $CH_2$ groups of alkyl, alkenyl, alkynyl and aralkyl which are not directly bound to the $OSO_2$ group may be replaced by O, 1,2-epoxyethylene, cyclopropylene, $OSO_2$ or $SO_2O$; in particular preferred $R^7$ is selected from methyl, ethyl, propyl, ethenyl, and 1-propyn-3-yl. In case $A^1$ is $[R^7—SO_3]$— no halide anions are used which have to be removed carefully if compound KA is used in lithium ion batteries, since halides have a detrimental effect on the life time of lithium ion batteries.

Especially preferred $A^1$ is an anion selected from $[R^7—SO_3]$— and $R^4$ and $R^7$ are same. Compounds $KA^1$ wherein $R^4$ and $R^7$ are same are easily prepared in one step as described below. The use of symmetrical educts for the preparation of $KA^1$ which are substituted twice by the same substituent $SOR^4$ in comparison to educts which are unsymmetrically substituted is simpler. The synthesis of $KA^1$ from educts substituted by halogen and $SOR^4$ is more complicated and expensive.

In a preferred embodiment of the preparation process K is a cation of formula (I), wherein X is N, $R^1$ and $R^2$ form together with the central X-atom a five-membered heterocycle, $R^3$ and $R^4$ are selected from $C_1$ to $C_6$ alkyl, and L is a —$(CH_2)_n$-chain with n=1, 2, 3 or 4;
A is an anion selected from bis(oxalato) borate and difluoro oxalato borate, preferred is bis(oxalato) borate;
$K^1$ is a cation selected from $[NR^8R^9R^{10}R^{11}]^+$ wherein $R^8$, $R^9$, and $R^{10}$ are selected independently from each other from $C_1$-$C_6$ alkyl or wherein $R^8$ and $R^9$ are linked and jointly selected from —$(CH_2)_4$— alkylene forming together with the central N-atom a five-membered heterocycle and $R^{11}$ is selected independently from $R^8$, $R^9$, and $R^{10}$ from H and $C_1$-$C_6$ alkyl, preferably $R^{11}$ is H; and
$A^1$ is an anion selected from $[R^7—SO_3]$— wherein $R^7$ is selected from $C_1$-$C_6$ alkyl.

$K^1A$ and $KA^1$ are brought into contact in the presence of a solvent or solvent mixture (i). Any solvent or solvent mixture suitable may be used, e.g. the solvent or solvent mixture (i) may be selected from $C_1$ to $C_6$ alcohols, di-$C_1$ to $C_6$ alkylethers, $C_1$ to $C_4$ carboxylic acid $C_1$ to $C_4$ alkylesters, di-$C_1$ to $C_4$ alkyl carbonates, acetonitrile and $C_1$ to $C_4$ ketones and mixtures thereof.

The term "$C_1$ to $C_6$ alcohol" means an alcohol containing 1 to 6 C-atoms and at least one alcoholic OH-group. Examples of $C_1$ to $C_6$ alcohols include methanol, ethanol, n-propanol, i-propanol and the like, preferred is methanol.

Examples of di-$C_1$-$C_6$-alkylethers are dimethylether, ethylmethylether, diethylether, diisopropylether, di-n-butylether, and methyl-tert-butylether, preferred is methyl-tert-butylether.

The term "$C_1$ to $C_4$ carboxylic acid $C_1$ to $C_4$ alkylester" means an ester of a carboxylic acid containing 1 to 4 C-atoms and an alcohol containing 1 to 4 C-atoms. Examples of $C_1$ to $C_4$ carboxylic acid $C_1$ to $C_4$ alkylester are methyl formate, ethyl formate, methyl acetate, ethyl acetate, methyl proprionate and methyl butanoate. Preferred are methyl acetate and ethyl acetate.

Di-$C_1$ to $C_4$ alkyl carbonates are acyclic organic carbonates, wherein each $C_1$ to $C_4$ alkyl group is selected independently from each other. Examples are diethyl carbonate (DEC), ethyl methyl carbonate (EMC), dimethyl carbonate (DMC), and methylpropyl carbonate. Preferred are diethyl carbonate (DEC), ethyl methyl carbonate (EMC), and dimethyl carbonate (DMC). Examples of $C_1$ to $C_4$ ketones are acetone and ethylmethylketone. Preferred is acetone.

Compound $KA^1$ is brought into contact with compound $K^1A$ in the presence of a solvent or solvent mixture (i). This step is also referred to as step (b). Step (b) may e.g. be conducted by preparing a mixture of $KA^1$ or $K^1A$ with the solvent or solvent mixture (i) and adding $K^1A$ or $KA^1$, respectively, or preparing a mixture of $KA^1$ and $K^1A$ and the solvent or solvent mixture (i) or by preparing a mixture of $KA^1$ with a first solvent or solvent mixture (i) and a mixture of $K^1A$ with a second solvent or solvent mixture (i) and bringing the two mixture into contact with each other, e.g. by adding one solution to the other and mixing, stirring and/or shaking. The first solvent or solvent mixture (i) and second solvent or solvent mixture (i) may be same or different. A mixture of compound $KA^1$, $K^1A$ or both with the solvent or solvent mixture (i) is preferably a solution of $KA^1$, $K^1A$ or both in the solvent or solvent mixture (i). A solution of a compound means herein that the compound is soluble in the solvent or solvent mixture at a concentration of at least 1 g/L at 25° C.

Preferably in step (b) a solution of $KA^1$ in a first solvent or solvent mixture (i) is brought into contact with a solution of $K^1A$ in a second solvent or solvent mixture (i). The first solvent or solvent mixture (i) and second solvent or solvent mixture (i) may be same or different. According to one embodiment, the first solvent or solvent mixture (i) and second solvent or solvent mixture (i) may be same.

During or after step (b) compounds KA or $K^1A^1$ are separated from each other. One possibility is to precipitate one of the two compounds KA or $K^1A^1$ while the other compound is maintained as solution in the solvent or solvent mixture (i). Afterwards the compound in precipitate form is separated from the solution of the other compound in the solvent or solvent mixture (i). Preferably compound KA is precipitated during or after step (b) and is separated from the mixture containing the solvent or solvent mixture (i) and $K^1A^1$ in dissolved form.

Precipitation of one of the two compounds KA or $K^1A^1$ may be induced for example by choosing the solvent or solvent mixture (i) present in the mixture obtained in step (b) such that one of the compounds KA or $K^1A^1$ is not or only partially soluble in the solvent or solvent mixture (i) present in the mixture obtained in step (b), preferably the solubility of either KA or $K^1A^1$ in the solvent or solvent mixture (i) present in the mixture obtained in step (b) is at maximum 10 mg/L at 25° C. It is also possible to add a non-solvent for one of KA or $K^1A^1$ to the mixture obtained in step (b) to amend the solubility of KA or $K^1$A1, respectively. Another possibility is to decrease the solubility of one of KA or $K^1A^1$ in the mixture obtained in step (b) by lowering the temperature of the mixture obtained in step (b).

Preferably compound KA is precipitated in the mixture obtained in step (b) during or after step (b), more preferred compound KA is precipitated during step (b) by choosing the solvent or solvent mixture (i) such that KA is not or only partially soluble in the solvent or solvent mixture (i) present in the mixture obtained in step (b) or compound KA is precipitated after step (b) by decreasing the solubility of KA in the mixture obtained in step (b) by decreasing the temperature of the mixture obtained in step (b).

For illustration purposes the different possible ways of precipitating selectively KA or $K^1A^1$ during after step (b) by adjusting the solvents is described in the following in respect of precipitating selectively KA. One alternative comprises using a first solvent (i) in which $K^1A$ and KA are soluble, using a second solvent (i) for $KA^1$ which is a solvent for $KA^1$ but a non-solvent for KA and choosing the ratio of the first solvent (i) to the second solvent (i) such that the resulting mixture of solvents (i) in step (b) constitutes a non-solvent for KA but a solvent for $K^1A^1$, i.e. KA is not or only partially soluble in the resulting mixture of solvents or is altered into a non-solvent for KA by decreasing the temperature of the mixture obtained in step (b) whereas $K^1A^1$ stays in the dissolved form. Instead of the first or second solvent (i) a solvent mixture (i) may be used, respectively.

An example for this process is shown in the experiments. For the preparation of 1-methyl-1-(2-((methylsulfonyl)oxy) ethyl)-pyrrolidinium bis(oxalatoborate) (KA) solutions of 1-methyl-1-(2-((methylsulfonyl)oxy)ethyl)-pyrrolidinium methansulfonate ($KA^1$) in methanol and triethylammonium bis(oxalatoborate) ($K^1A$) in methanol are mixed. Methanol is a non-solvent for 1-methyl-1-(2-((methylsulfonyl)oxy) ethyl)-pyrrolidinium bis(oxalatoborate) (KA), but a solvent for 1-methyl-1-(2-((methylsulfonyl)oxy)ethyl)-pyrrolidinium methansulfonate ($KA^1$), triethylammonium bis(oxalatoborate) ($K^1A^1$), and triethylammonium methansulfonate ($K^1A^1$).

In a preferred embodiment anion A is bis(oxalato) borate. If A is bis(oxalato) borate it is preferred to use a compound $K^1A$ in step (b) which was prepared by reaction of oxalic acid, $B(OH)_3$ and $NR^8R^9R^{10}$. In this case compound $K^1A$ is selected from $[HNR^8R^9R^{10}]^+$ bis(oxalato) borate. The reaction of oxalic acid, $B(OH)_3$ and $NR^8R^9R^{10}$ may be carried out in a solvent or solvent mixture and the water generated is removed by distillation during the reacting to shift the reaction equilibrium to bis(oxalato) borate. The reaction may be carried out in analogy to the preparation of HBOB described in WO 02/068433 A1.

A preferred embodiment of the present process wherein A is bis(oxalato) borate comprises the steps
(a2) preparing a compound $K^1A$ by reacting oxalic acid, $B(OH)_3$ and $NR^8R^9R^{10}$; and
(b) bringing into contact compound $K^1A$ obtained in step (a2) and compound $KA^1$ and in the presence of a solvent or solvent mixture (i).

In another preferred embodiment a compound $KA^1$ is used in step (b) which was prepared by reaction of $R^4SO_2$—O—L—O—$SO_2R^7$ with $NR^1R^2R^3$. In case $R^4$ and $R^7$ are same it is preferred to use $R^4SO_2$—O—L—O—$SO_2R^7$ for the preparation of $KA^1$ which was prepared by reaction of HO—L—OH with $R^4SO_2C_1$.

A preferred embodiment of the present process comprises the steps
(a1) preparing a compound $KA^1$ by reacting $R^4SO_2$—O—L—O—$SO_2R^7$ with $NR^1R^2R^3$; and
(b) bringing into contact compound $KA^1$ obtained in step (a1) and compound $K^1A$ and in the presence of a solvent or solvent mixture (i);

A preferred embodiment of the present process wherein $R^4$ and $R^7$ are same comprises the steps
(a0) Preparing a compound $R^4SO_2$—O—L—O—$SO_2R^7$ by reaction of HO—L—OH with $R^4SO_2C_1$;
(a1) preparing a compound $KA^1$ by reacting $R^4SO_2$—O—L—O—$SO_2R^7$ obtained in step (a0) with $NR^1R^2R^3$; and
(b) bringing into contact compound $KA^1$ obtained in step (a1) and compound $K^1A$ obtained in step (a2) and in the presence of a solvent or solvent mixture (i).

A further preferred embodiment of the present process wherein A is bis(oxalato) borate comprises the steps
(a1) preparing a compound $KA^1$ by reacting $R^4SO_2$—O—L—O—$SO_2R^7$ with $NR^1R^2R^3$;
(a2) preparing a compound $K^1A$ by reacting oxalic acid, $B(OH)_3$ and $NR^8R^9R^{10}$; and
(b) bringing into contact compound $KA^1$ obtained in step (a1) and compound $K^1A$ obtained in step (a2) in the presence of a solvent or solvent mixture (i).

In an embodiment which is also preferred A is bis(oxalato) borate and $R^4$ and $R^7$ are same and the process comprises the steps
(a0) preparing a compound $R^4SO_2$—O—L—O—$SO_2R^7$ by reaction of HO—L—OH with $R^4SO_2C_1$;
(a1) preparing a compound $KA^1$ by reacting $R^4SO_2$—O—L—O—$SO_2R^7$ obtained in step (a0) with $NR^1R^2R^3$;
(a2) preparing a compound $K^1A$ by reacting oxalic acid, $B(OH)_3$ and $NR^8R^9R^{10}$; and
(b) bringing into contact compound $KA^1$ obtained in step (a1) and compound $K^1A$ obtained in step (a2) and in the presence of a solvent or solvent mixture (i).

The invention is illustrated by the examples which follow, which do not, however, restrict the invention.

I Preparation of 1-methyl-1-(2-((methylsulfonyl) oxy)ethyl)-pyrrolidinium methansulfonate Ia Preparation of 1,2-ethane Diol Bismethanesulfonate

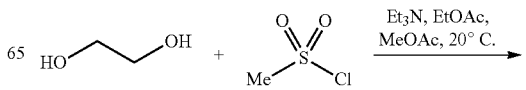

-continued

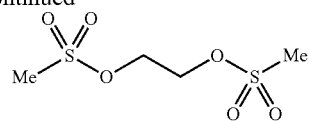

EXAMPLE 1

A mixture of 40 g ethylene glycol, 163 g triethylamine, 350 g ethyl acetate and 60.5 g methyl acetate was prepared at 25° C. and was cooled to 0° C. 170 g methane sulfonyl chloride was added in a controlled manner to ensure, that the temperature of the mixture did not exceed 25° C. The suspension obtained was stirred for additional 60 min at 25° C. 325 g deionized water was added and the phases were separated. The solvents were removed from the organic phase at 65° C. in vacuum and the obtained raw product was used in the next step.

Isolated yield (i.e. yield of isolated product) was 85%, purity determined by gas chromatography (GC analysis) was 94 wt.-%.

EXAMPLE 2

A mixture of 0.32 kg ethylene glycol, 1.30 kg triethylamine, 3.59 kg ethyl acetate and 0.48 kg methyl acetate was prepared and cooled to −10° C. 1.21 kg methanesulfonyl chloride was added in a controlled manner to ensure, that the temperature of the mixture did not exceed 4° C. The obtained suspension was stirred for additional 15 min. 2.1 kg deionized water was added and the phases were separated. The organic phase was sequentially washed with additional portions of water, before the solvents were removed at 65° C. in vacuum. The raw product was used in the next step, without further purification.

Isolated yield: 92%; purity (GC Analysis): 98.6 wt %

EXAMPLE 3

1,2-ethane diol bismethanesulfonate was prepared according to example 1. The crude material was further purified by crystallization from methyl-tert-butyl-ether and acetone at 55° C. in order to obtain the product as colorless crystalline material.

Isolated yield: 60%; purity (GC Analysis): 98.8 wt %

Ib Preparation of 1-methyl-1-(2-((methylsulfonyl)oxy)ethyl)-pyrrolidinium methansulfonate

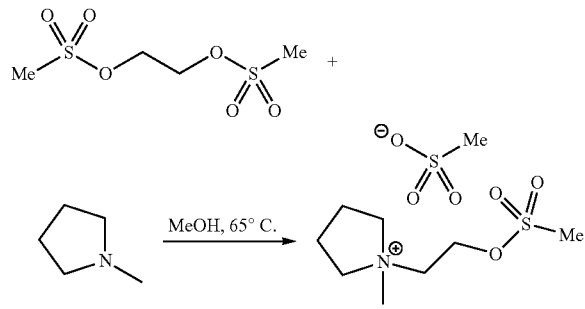

EXAMPLE 4

131 g 1,2-ethane diol bismethanesulfonate obtained according to reaction Ia and 360 mL methanol were stirred for 10 min resulting in a clear solution. The solution was heated to 65° C. and 51 g N-methylpyrrolidine was added. The reaction mixture was stirred for 16 h at 65° C. Solvent and volatile compounds were removed by distillation under vacuum at 60° C. Afterwards methanol was added and the solution of 1-methyl-1-(2-((methylsulfonyl)oxy)ethyl)-pyrrolidinium methansulfonate in methanol can be used directly in step IV a.

EXAMPLE 5

1.03 kg 1,2-ethane diol bismethanesulfonate, obtained according to reaction Ia, was dissolved in 2.2 kg methanol and heated to 60° C. 0.42 kg N-methylpyrrolidine was added and stirring was continued for 12-17 h. Crude 1-methyl-1-(2-((methylsulfonyl)oxy)ethyl)-pyrrolidinium methansulfonate in methanol can be used directly in IVa, without further purification.

EXAMPLE 6

256 g 1,2-ethane diol bismethanesulfonate, obtained according to reaction Ia, was dissolved in 700 mL methanol and heated to 40° C. 119 g N-methylpyrrolidine was added and stirring was continued for 48-60 h. Crude 1-methyl-1-(2-((methylsulfonyl)oxy)ethyl)-pyrrolidinium methansulfonate in methanol can be used directly in IVa, without further purification.

EXAMPLE 7

250 g 1,2-ethane diol bismethanesulfonate, obtained according to reaction Ia, was dissolved in 800 mL acetone and 20 mL methanol and heated to 60° C. 119 g N-methylpyrrolidine was added and stirring was continued for 12-17 h. After cooling, the suspension was filtered, the residue sequentially washed with 100 mL acetone and dried in vacuum. 1-methyl-1-(2-((methylsulfonyl)oxy)ethyl)-pyrrolidinium methansulfonate was obtained as off-white powder in 73% yield.

EXAMPLE 8

250 g 1,2-ethane diol bismethanesulfonate, obtained according to reaction Ia, was dissolved in 800 mL acetone and heated to 60° C. 119 g N-methylpyrrolidine was added and stirring was continued for 12-17 h. After cooling, the suspension was filtered, the residue sequentially washed with 100 mL acetone and dried in vacuum. 1-methyl-1-(2-((methylsulfonyl)oxy)ethyl)pyrrolidinium methansulfonate was obtained as off-white powder in 85% yield.

EXAMPLE 9

254 g 1,2-ethane diol bismethanesulfonate, obtained according to reaction Ia, was dissolved in 570 mL acetonitrile and heated to 90° C. 128 g N-methylpyrrolidine was added and stirring was continued for 3 h. 570 mL acetone were added, before the reaction mixture was cooled to 0° C. and stirred over night. The suspension was filtered, the residue sequentially washed with 500 mL acetone and dried in vacuum. 1-methyl-1-(2-((methylsulfonyl)oxy)ethyl)-pyrrolidinium methansulfonate was obtained as off-white powder in 90% yield.

II Preparation of triethylammonium bis(oxalatoborate)

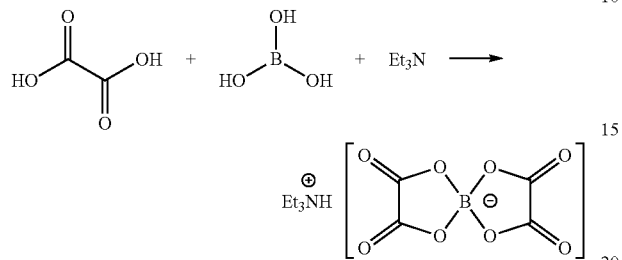

EXAMPLE 10

179 g oxalic acid dihydrate and 44 g boric acid were mixed with 70 mL methanol and homogenized. 72 g triethylamine was added to this suspension. The reaction mixture was stirred at 120 to 130° C. while volatile components were removed by distillation for about 2 h. The reaction mixture was cooled down to room temperature and vented with nitrogen. Methanol was added and the mixture was stirred for 1 h at room temperature. The solution of triethylammonium bis(oxalatoborate) was used in IVa.

III Preparation of methylimidazolium bis(oxalatoborate)

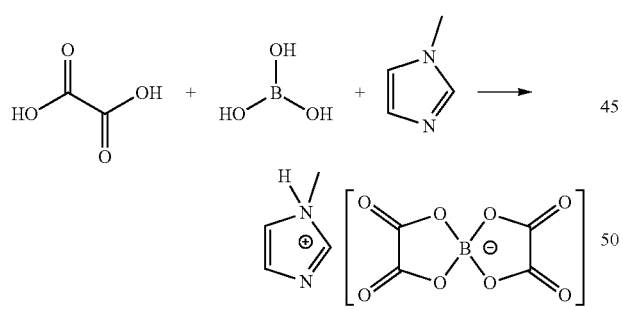

EXAMPLE 11

14 g oxalic acid dihydrate and 4.8 g boric acid were mixed with 50 mL methanol and homogenized. 6.4 g methylimidazole was added to this suspension. The reaction mixture was stirred at 60° C. while stirring volatile components were removed by distillation und vacuum up to 150 mbar. The reaction mixture was further concentrated under vacuum at 120° C. and was died completely under 0.5 mbar at 135° C. Methylimidazolium bis(oxalatoborate) was obtained as beige solid with a yield of 80.3%.

IV Preparation of 1-methyl-1-(2-((methylsulfonyl)oxy)ethyl)-pyrrolidinium bis(oxalatoborate)

IVa Preparation via triethylammonium bis(oxalatoborate)

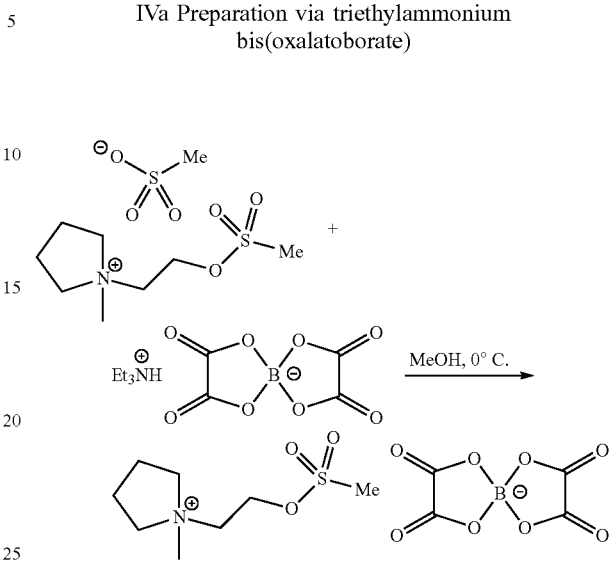

EXAMPLE 12

570 g of the methanolic solution of 1-methyl-1-(2-((methylsulfonyl)oxy)ethyl)-pyrrolidinium methansulfonate obtained in Ib were cooled under vigorous stirring to 0° C. and seed crystals of 1-methyl-1-(2-((methylsulfonyl)oxy)ethyl)-pyrrolidinium bis(oxalatoborate) were added. Afterwards 579 g of the methanolic solution of triethylammonium bis(oxalatoborate) obtained in II was added dropwise within 45 min. The mixture was stirred at 0° C. for 1 h before the cooled suspension obtained was filtrated. The filter cake consisting essentially of 1-methyl-1-(2-((methylsulfonyl)oxy)ethyl)-pyrrolidinium bis(oxalatoborate) was rinsed several times with cold methanol and dried in vacuum under small nitrogen flow. 1-methyl-1-(2-((methylsulfonyl)oxy)ethyl)-pyrrolidinium bis(oxalatoborate) was obtained as colorless solid in a yield of 59.3% based on the ethylene glycol used for the preparation of 1,2-ethane diol bismethanesulfonate in step Ia.

IV b Preparation via methylimidazolium bis(oxalatoborate)

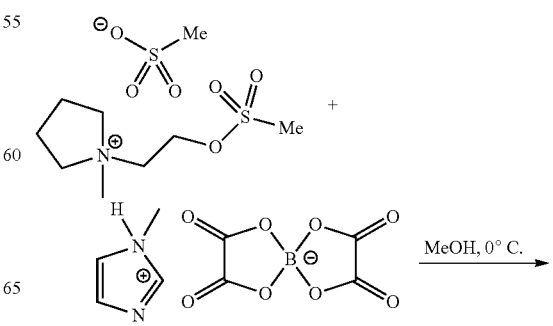

-continued

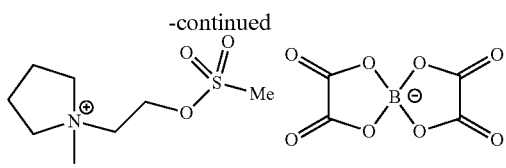

EXAMPLE 13

14.3 g of 1-methyl-1-(2-((methylsulfonyl)oxy)ethyl)-pyrrolidinium methansulfonate prepared as described in I was dissolved in 50 mL methanol under vigorous stirring and cooled down to 0° C. A methanolic solution of 15 g methylimidazolium bis(oxalatoborate) was added within 45 min dropwise. The mixture was stirred for 1 h at 0° C. The suspension obtained was filtrated. The filtercake consisting essentially of 1-methyl-1-(2-((methylsulfonyl)oxy)ethyl)-pyrrolidinium bis(oxalatoborate) was rinsed with cold methanol several times and dried in vacuum under small nitrogen flow. The product was obtained as colorless solid with a yield of 42.1% based on the ethylene glycol used for the preparation of 1,2-ethane diol bismethanesulfonate in step Ia.

V Preparation of 1-methyl-1-(2-((methylsulfonyl)oxy)ethyl)-pyrrolidinium difluoro(oxalatoborate)

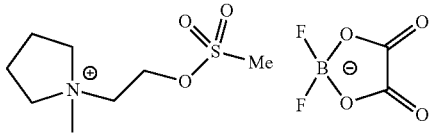

EXAMPLE 14

30 g of 1-methyl-1-(2-((methylsulfonyl)oxy)ethyl)-pyrrolidinium methansulfonate was dissolved in 100 mL methanol, charged with seed crystals of 1-methyl-1-(2-((methylsulfonyl)oxy)ethyl)-pyrrolidinium difluoro(oxalatoborate) and cooled in an ice-bath. A solution of 24 g triethylammonium difluoro(oxalatoborate) in acetonitrile was added dropwise, followed by stirring for an additional hour. The suspension was filtered and the residue sequentially washed with portions of cold methanol. 1-methyl-1-(2-((methylsulfonyl)oxy)ethyl)-pyrrolidinium difluoro(oxalatoborate) was obtained as colorless solid in 48% yield.

EXAMPLE 15

30 g of 1-methyl-1-(2-((methylsulfonyl)oxy)ethyl)-pyrrolidinium methansulfonate was dissolved in 100 mL methanol, charged with seed crystals of 1-methyl-1-(2-((methylsulfonyl)oxy)ethyl)-pyrrolidinium difluoro(oxalatoborate) and cooled in an ice-bath. A solution of 24 g triethylammonium difluoro(oxalatoborate) in methanol was added dropwise, followed by stirring for an additional hour. The suspension was filtered and the residue sequentially washed with portions of cold methanol. 1-methyl-1-(2-((methylsulfonyl)oxy)ethyl)-pyrrolidinium difluoro(oxalatoborate) was obtained as colorless solid in 76% yield.

EXAMPLE 16

30 g of 1-methyl-1-(2-((methylsulfonyl)oxy)ethyl)-pyrrolidinium methansulfonate was dissolved in 100 mL methanol, charged with seed crystals of 1-methyl-1-(2-((methylsulfonyl)oxy)ethyl)-pyrrolidinium difluoro(oxalatoborate) and cooled in an ice-bath. A solution of 24 g triethylammonium difluoro(oxalatoborate) in acetone was added dropwise, followed by stirring for an additional hour. The suspension was filtered and the residue sequentially washed with portions of cold methanol. 1-methyl-1-(2-((methylsulfonyl)oxy)ethyl)-pyrrolidinium difluoro(oxalatoborate) was obtained as colorless solid in 64% yield.

The invention claimed is:

1. A process of making 1-methyl-1(2-((methylsulfonyl)oxy)ethyl-pyrrolidinium bis(oxalatoborate) comprising contacting 1-methyl-1(2-((methylsulfonyl)oxy)ethyl-pyrrolidinium methanesulfonate with triethylammonium bis(oxalatoborate) in the presence of a solvent or a solvent mixture.

2. The process of claim 1, wherein the solvent is methanol.

3. The process of claim 2, wherein both 1-methyl-1(2-((methylsulfonyl)oxy)ethyl-pyrrolidinium methanesulfonate and triethylammonium bis(oxalatoborate) are dissolved in methanol.

4. The process of claim 3, wherein 1-methyl-1(2-((methylsulfonyl)oxy)ethyl-pyrrolidinium methanesulfonate is contacted with triethylammonium bis(oxalatoborate) at 0° C.

5. A process of making 1-methyl-1(2-((methylsulfonyl)oxy)ethyl-pyrrolidinium bis(oxalatoborate), comprising contacting 1-methyl-1(2-((methylsulfonyl)oxy)ethyl-pyrrolidinium methanesulfonate with methylimidazolium bis(oxalatoborate) in the presence of a solvent or a solvent mixture.

6. The process of claim 5, wherein the solvent is methanol.

7. The process of claim 6, wherein 1-methyl-1(2-((methylsulfonyl)oxy)ethyl-pyrrolidinium methanesulfonate is contacted with methylimidazolium bis(oxalatoborate) at 0° C.

8. The process of claim 7, wherein both 1-methyl-1(2-((methylsulfonyl)oxy)ethyl-pyrrolidinium methanesulfonate and methylimidazolium bis(oxalatoborate) are dissolved in methanol.

9. A process of making 1-methyl-1(2-((methylsulfonyl)oxy)ethyl-pyrrolidinium difluoro(oxalatoborate), the process comprising contacting 1-methyl-1(2-((methylsulfonyl)oxy)ethyl-pyrrolidinium methanesulfonate with triethylammonium difluoro(oxalatoborate) in a solvent or a solvent mixture.

10. The process of claim 9, wherein the solvent is methanol and the solvent mixture is methanol and acetonitrile or methanol and acetone.

11. The process of claim 10, wherein 1-methyl-1(2-((methylsulfonyl)oxy)ethyl-pyrrolidinium methanesulfonate is contacted with triethylammonium difluoro(oxalatoborate) at 0° C.

12. The process of claim 11, wherein both 1-methyl-1(2-((methylsulfonyl)oxy)ethyl-pyrrolidinium methanesulfonate and triethylammonium difluoro(oxalatoborate) are dissolved in methanol.

13. The process of claim 11, wherein 1-methyl-1(2-((methylsulfonyl)oxy)ethyl-pyrrolidinium methanesulfonate is dissolved in methanol and triethylammonium difluoro(oxalatoborate) is dissolved in acetonitrile.

14. The process of claim 11, wherein 1-methyl-1(2-((methylsulfonyl)oxy)ethyl-pyrrolidinium methanesulfonate is dissolved in methanol and triethylammonium difluoro(oxalatoborate) is dissolved in acetone.

* * * * *